(12) United States Patent
Tarassenko et al.

(10) Patent No.: US 8,290,575 B2
(45) Date of Patent: Oct. 16, 2012

(54) BIOMEDICAL SIGNAL MORPHOLOGY ANALYSIS METHOD

(75) Inventors: Lionel Tarassenko, Oxford (GB); Alan Patterson, Oxford (GB); Iain Guy Strachan, Oxon (GB)

(73) Assignee: OBS Medical Limited, Abingdon, Oxon (GB)

( * ) Notice: Subject to any disclaimer, the term of this patent is extended or adjusted under 35 U.S.C. 154(b) by 612 days.

(21) Appl. No.: 12/517,136

(22) PCT Filed: Nov. 30, 2007

(86) PCT No.: PCT/GB2007/004617
§ 371 (c)(1),
(2), (4) Date: Oct. 2, 2009

(87) PCT Pub. No.: WO2008/065432
PCT Pub. Date: Jun. 5, 2008

(65) Prior Publication Data
US 2010/0049069 A1     Feb. 25, 2010

(30) Foreign Application Priority Data

Dec. 1, 2006   (GB) .................................. 0624085.7

(51) Int. Cl.
*A61B 5/04*     (2006.01)
(52) U.S. Cl. ...................................................... 600/512
(58) Field of Classification Search .................. 600/512
See application file for complete search history.

(56) References Cited

U.S. PATENT DOCUMENTS 5,560,369 A    10/1996 McClure et al.
2003/0060724 A1   3/2003 Thiagarajan et al.
2003/0204146 A1  10/2003 Carlson
2005/0234357 A1  10/2005 Xue et al.
2005/0234363 A1  10/2005 Xue (Continued)

FOREIGN PATENT DOCUMENTS

WO   WO 2005/107587     11/2005

OTHER PUBLICATIONS

Hughes et al, "Markov Models for Automated ECG Interval Analysis", (2004), vol. 16, Thrun S, Saul L & Scholkopf B (eds), MIT Press.

(Continued)

*Primary Examiner* — George Manuel
*Assistant Examiner* — Robert N Wieland
(74) *Attorney, Agent, or Firm* — Nixon & Vanderhye P.C.

(57) ABSTRACT

A way of quantifying the shape of an ECG waveform is disclosed by detecting the JT segment using two Hidden Markov Models and calculating the analytic signal of the JT segment. Parameters calculated from the analytic signal are used as shape descriptors for the JT segment. The shape descriptors may be displayed in a dimensionality-reduced mapping. Templates representing characteristic shapes can be produced by finding cluster centers in the shape descriptor space, and the novelty of new waveforms can be quantified by comparing the position in shape descriptor space of new shape descriptors to a predefined normal training set or to previously encountered waveforms. Novel shape descriptors can be used to retrieve the corresponding waveforms, and templates of such novel shapes can be created by averaging such waveforms, using dynamic time warping to allow for variations in heart rate. The templates can be manually segmented and the manual segmentation propagated back into other waveforms having similar shape descriptors.

34 Claims, 14 Drawing Sheets

U.S. PATENT DOCUMENTS

2007/0273504 A1* 11/2007 Tran .................... 340/539.12
2008/0132799 A1*  6/2008 Xue ........................ 600/509

OTHER PUBLICATIONS

International Search Report for PCT/GB2007/004617 mailed Mar. 14, 2008.
Written Opinion of the International Searching Authority for PCT/GB2007/004617, mailed Mar. 14, 2008.
UK Search Report for GB Application No. 0624085.7, dated Apr. 3, 2007.
Hughes, N. P. et al., "Automated QT Interval Analysis with Confidence Measures", Computers in Cardiology, 2004, (Sep. 19-22, 2004), pp. 765-768.

* cited by examiner

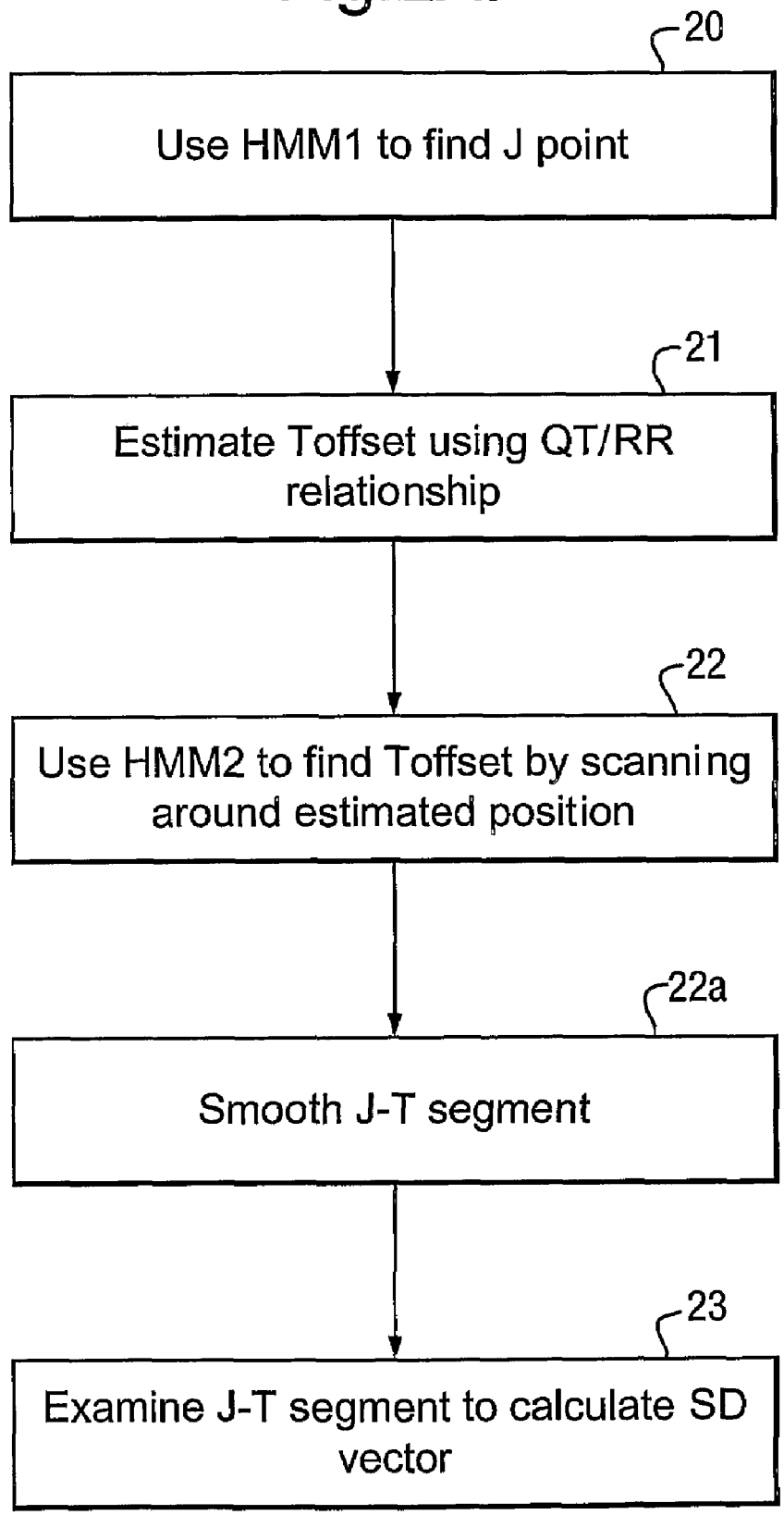

Minute 16

Minute 184

BIOMEDICAL SIGNAL MORPHOLOGY ANALYSIS METHOD

This application is the U.S. national phase of International Application No. PCT/GB2007/004617 filed 30 Nov. 2007, which designated the U.S. and claims priority to Great Britain Application No. 0624085.7 filed 1 Dec. 2006, the entire contents of each of which are hereby incorporated by reference.

The present invention concerns a method for the analysis of a biomedical signal such as an electrocardiogram (ECG) or other biomedical signal.

There are a variety of biomedical signals, i.e. signals representative of the state or condition of a human or animal, which are obtained invasively or non-invasively by the use of monitoring instrumentation. Typical examples include electrocardiograms (ECG), electroencephalograms (EEG), electroencephalograms (EEG), beat-to-beat blood pressure, the photoplethysmograph (PPG), impedance plethysmograph, respiration rate or impedance pneumogram, and blood oxygen saturation which all have regularly repeating patterns. These signals are typically examined by experts to determine, for example, the state of health of the human or animal, the effect of some therapy, for example, a drug, on the human or animal and so on. Such expert analysis is, however, time consuming and expensive. Considerable efforts have therefore been made over the past few years to provide automated techniques for analysing biomedical signals. Such signals are often noisy, complex and highly variable in time and from individual to individual. Automated analysis is therefore difficult, and the large amount of data which can be generated by signal recordings from even one individual over an extended period can make it impractical to analyse all of the data even using computers with fast processors.

An example of an automated signal analysis method for segmentation of electrocardiograms is disclosed in WO 2005/107587. That document discloses the use of a Hidden Markov Model to segment individual heartbeats in an electrocardiogram (ECG). The ECG (also known by the acronym EKG) is an important non-invasive signal which measures the electrical activity of the heart.

Each individual heartbeat is comprised of a number of distinct cardiological stages, which in turn give rise to a set of distinct features in the ECG waveform. These features represent either depolarization (electrical discharging) or repolarization (electrical recharging) of the muscle cells in particular regions of the heart. FIG. 1 shows a human ECG waveform and the associated features. The standard features of the ECG waveform are the P wave, the QRS complex and the T wave. Additionally a small U wave (following the T wave) is occasionally present.

The cardiac cycle begins with the P wave (the start and end points of which are referred to as $P_{On}$ and $P_{offset}$), which corresponds to the period of atrial depolarization in the heart. This is followed by the QRS complex, which is generally the most recognisable feature of an ECG waveform, and corresponds to the period of ventricular depolarization (which masks the atrial repolarization). The start and end points of the QRS complex are referred to as the $Q_{onset}$ and J points. The T wave follows the QRS complex and corresponds to the period of ventricular repolarization. The end point of the T wave is referred to as $T_{offset}$ and represents the end of the cardiac cycle (presuming the absence of a U wave). By examining the ECG signal in detail it is possible to derive a number of informative measurements from the characteristic ECG waveform. These can then be used to assess cardiac condition and detect changes or potential abnormalities present in the cardiac rhythm.

A particularly important measurement is the "QT interval", which is defined as the time from the start of the QRS complex to the end of the T wave, i.e. $T_{offset}-Q_{onset}$. This timing interval corresponds to the total duration of the electrical activity (both depolarization and repolarization) in the ventricles.

The QT interval is particularly significant since it is a good indicator of certain medical conditions, and it also has to be monitored in volunteers testing new pharmacological substances in clinical trials. In the past such volunteers would have their ECGs monitored and recorded for relatively short times (for example 10 seconds or so) at regular intervals during a clinical trial. For example in connection with the administration of an experimental drug, 10 second ECG recordings might be made on administration of the drug (time point zero), at 30 minutes, one hour, 1.5 hours and so on up to one day later, but typically decreasing in frequency after the first six hours. Typically, as a control, ECG recordings would also be made at the corresponding times on a day when the volunteer is not administered with the drug, and on a day when the volunteer is administered with a placebo. The effect of the drug on the volunteer's heart, for example whether it lengthens the QT interval, and by how much, will be appraised by experts reviewing the short ECG recordings.

More recently, though, concerns that recording short periods of ECG at spaced intervals through the day might miss certain effects has led to continuous recording of all twelve channels (a so-called Holter recording). This hugely increases the amount of ECG data. While manual analysis is possible with short duration recordings at regularly spaced intervals as above, with a continuous Holter recording, analysis of the 24 hours would require of the order of 100,000 beats (60 bpm×60 minutes×24 hours=86,400) to be analysed per channel. This makes existing methods of expert analysis, and indeed many methods of automated analysis, impractical.

Although automatic analysis techniques, such as that disclosed in WO 2005/107587, can reduce the burden, it has been found that on 24 hour channel ECG recordings there can be as many as 50,000 beats recorded which the automated segmentation algorithms cannot segment with a reasonable level of accuracy or reliability.

While with the traditional ten-second ECG recordings at 30 min or 1 hour intervals during the day the number of low confidence beats for a day might be 100, which could be presented to a clinician for manual segmentation, it is clearly impractical to do so for 50,000 beats. Further, it would not be safe simply to reject such a high proportion of beats as the low confidence cannot certainly be ascribed to noise or artefact, but maybe caused by a variation from normal cardiac activity which is of clinical significance or interest.

An additional problem which occurs in analysis of ECGs is that the QT interval varies with heart rate. So decreased heart rate leads to increased QT interval. The increase and decrease in QT interval associated with heart rate changes is much greater than the change caused by a pharmacological substance. The heart rate also varies periodically with the breathing cycle, and this periodic change also affects the QT interval. Thus values of the QT interval measured from an ECG are usually corrected by dividing the measured QT interval by the cube root or square root of the beat to beat interval (period from one R peak to the next) in seconds. This correction is not, however, particularly accurate.

A first aspect of the present invention provides a method of analysing a biomedical signal having a repetitive signal feature, comprising the steps of segmenting each of a plurality of said repetitive signal features in the biomedical signal, analysing one or more of the segments to find the values of a plurality of parameters describing the shape of said one or more of the segments, recording the values, and tracking changes in the said values through the biomedical signal.

Thus this aspect of the invention gives the ability to track automatically the shape or "morphology" of segments of a biomedical signal through time.

The biomedical signal may, for example, be an electrocardiogram in which the repetitive signal feature is the heartbeat. Thus rather than relying on a clinician to monitor shape changes in the ECG waveform, such changes may be measured and tracked automatically.

Conveniently in the case of analysing ECGs the T-wave of the heartbeat is analysed, this being the segment from the J point to the $T_{offset}$ point.

The J point may be detected by the use of a Hidden Markov Model comprising a state model for the waveform before and after the J point. Similarly the $T_{offset}$ point can be detected by the use of a Hidden Markov Model comprising state models for the T wave and the waveform before and after $T_{offset}$.

In locating the $T_{offset}$ point it is preferred to maintain from beat to beat through the electrocardiogram an estimate of the QT interval based on a relationship between the QT interval and the heartrate, and to estimate the position of $T_{offset}$ from the estimated QT interval and R wave peak (found by a standard algorithm). The Hidden Markov Model to detect the $T_{offset}$ point can then be applied to a section of the electrocardiogram defined with respect to the estimated $T_{offset}$ position. This reduces the extent of the ECG which has to be scanned to find the $T_{offset}$ position and thus increases the speed of the algorithm.

A Kalman filter or other predictive system is used to maintain the estimate of the $T_{offset}$ point location from beat to beat.

Of course other ways of segmenting the T-wave in the ECG, or other desired portion of a biomedical signal, may be used.

The plurality of parameters describing the shape of the segment of the biomedical signal can constitute components of a shape descriptor vector for that segment. It is then possible to consider different shapes as being represented by different points in the shape descriptor vector space.

For example, it is possible to define normality for the shape of the waveform by defining a normal region in shape descriptor space. In a batch learning process normality can be defined by using a training set of biomedical signals considered to be normal.

A new waveform can be compared to normality by comparing the position of its shape descriptor vector in shape descriptor vector space and the defined normality. The degree of novelty of a new waveform may be based on a distance measure (for example Euclidean distance) between its shape descriptor vector and the nearest shape descriptor vector representing normality (i.e. of the training set), or the density of points in shape descriptor vector space can be calculated, and then the probability of normality of a given shape descriptor vector can be calculated from that.

A morphology index value describing the degree of novelty of a given waveform can be defined on the basis of the difference in shape descriptor vectors. The morphology index value can be displayed as a function of time for the extent of the recording of the biomedical signal.

It is also possible to apply a dimensionality reduction mapping to the shape descriptor vectors, which allows the shape descriptor vectors to be displayed on a two dimensional display, for example the dimensionality reduction mapping being one of those that preserves as closely as possible the spatial relationship between the shape descriptor vectors in the original space (such the Neuroscale mapping, an analytic form having similar properties to the Sammon Map, see for example http://citeseer.ist.psu.edu/lowe97neuroscale.html).

Where the biomedical signal is an electrocardiogram it may be corrected for variations in heart rate caused by the breathing cycle by means of dynamic time warping.

Thus where a biomedical signal has been segmented automatically, signals whose segmentation confidence is low can be presented for manual segmentation. Preferably, though, the number of signals requiring manual segmentation is reduced by defining templates representative of different families of signal, with some similarity between the members of each family.

Where a biomedical signal is encountered with repetitive signal features whose shape descriptor parameters depart from predefined normality by more than a predetermined threshold, or if the waveform was segmented, but with confidence less than a predetermined threshold, and greater than a rejection threshold, it is preferred to provide for manual segmentation of such biomedical signals.

Preferably the number of signals requiring manual segmentation is reduced by defining a template which is representative of the shape of the signal for a plurality of signal features having similar shape descriptor vectors. Thus a group or family of signal features may be defined whose shape descriptor vectors are within a predetermined distance of each other in shape descriptor vector space, the group being outside the normal region i.e. being characterised as novel with respect to normal shapes.

Preferably the group only comprises shape descriptor vectors of signal features which are temporally localised, and one member of the group is taken and a template generated from the corresponding signal feature together with a number of its adjacent signal features in the signal recording. This means that the template is not prepared from waveforms of similar, but novel, shape which occur at very different times during the signal recording, but instead it is prepared from waveforms of similar but novel shape which are also temporally localised.

The template is preferably displayed for manual segmentation, that is to say a clinician can study the displayed waveform and mark the start and end of the various stages. The segmentation of the template can then be propagated back onto each of the waveforms whose shape descriptor vectors are in the group corresponding to that template.

Thus with this aspect of the invention the clinician is required to segment only a relatively few templates corresponding to different families of waveforms with this segmentation being applied automatically to all of the waveforms corresponding to that template.

It is, of course, possible for the manual segmentation to be used to re-train an algorithm (e.g. the Hidden Markov Models) used for the automatic segmentation, and for newly segmented waveforms of novel shape to be included in the training database.

The above techniques may also be applied in an online learning mode in which a signal or recording comprising a series of waveforms is continuously analysed as it is generated or reproduced, with templates being generated as required. Thus an initial portion of the signal or recording is used to generate a first template representative of the shape of the waveforms in that period. The template can simply be an average of the waveforms in that period. The shape of each succeeding waveform is then checked against that template, and if there is a change in shape which exceeds a predetermined threshold, that waveform, or a group of successive waveforms of similar changed shape, is used to generate a new template. Successive waveforms are then tested against the two templates, further significant changes in shape generating further templates. The thresholds are set empirically to control the number of templates generated. The templates may then be reviewed by an expert and annotations, segmentations and the like, may be propagated back into the individual waveforms for which that template is the closest match as described above.

The invention may be embodied in a computer program for executing the method on a computer system and the invention extends to such a program, to a storage medium carrying the program, and to a computer system programmed to execute the method.

The invention will be further described by way of example with reference to the accompanying drawings, in which.

Figure 2B:
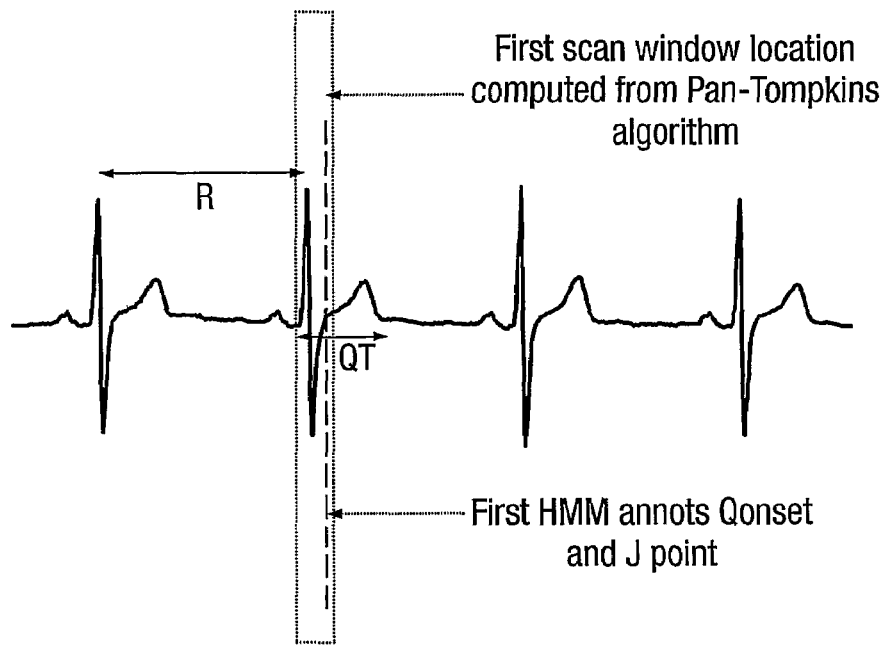
FIG. 2A is a flow diagram illustrating one embodiment of the invention for segmenting part of an ECG waveform.
Figure 3:
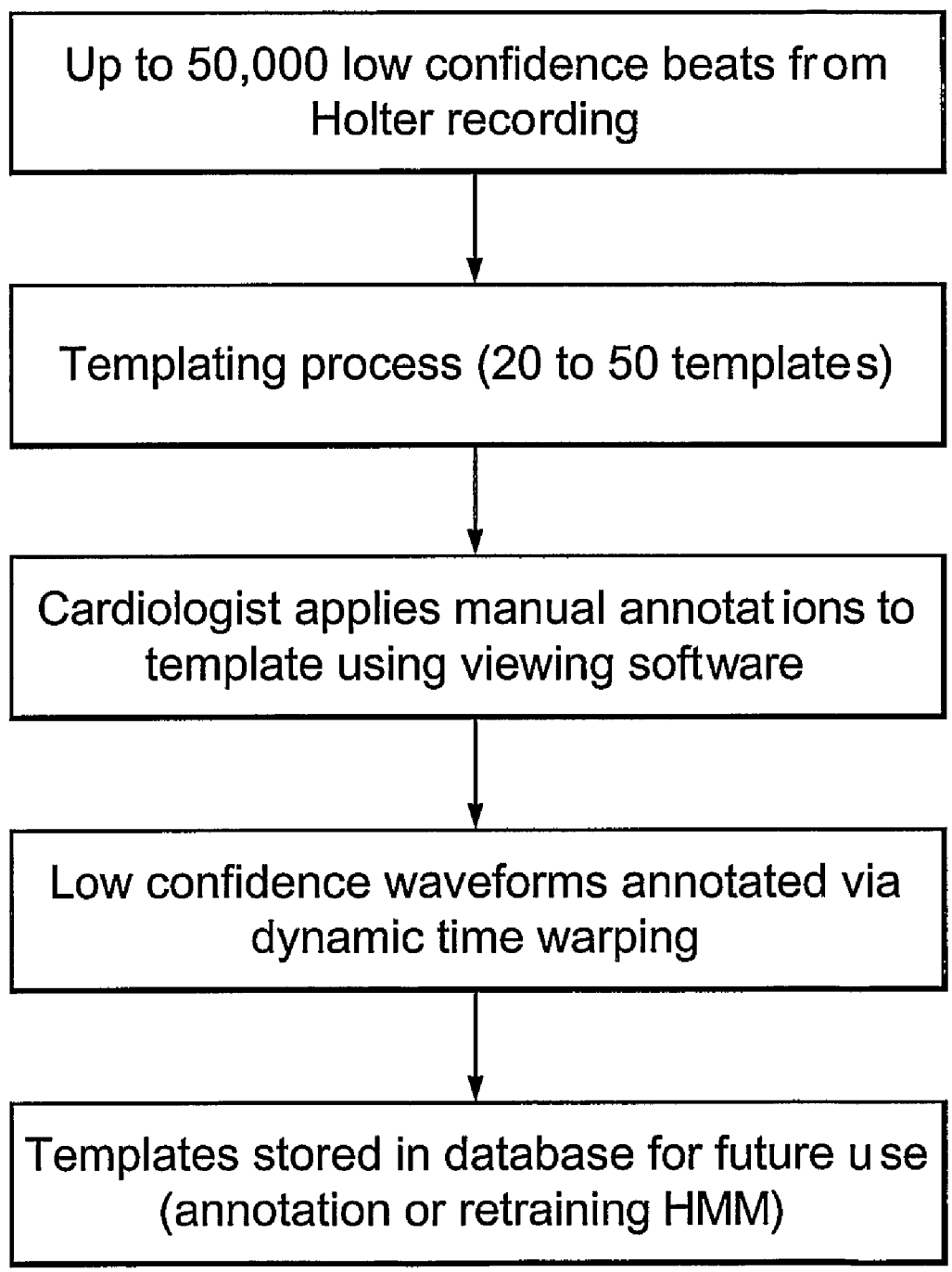
Figure 4:
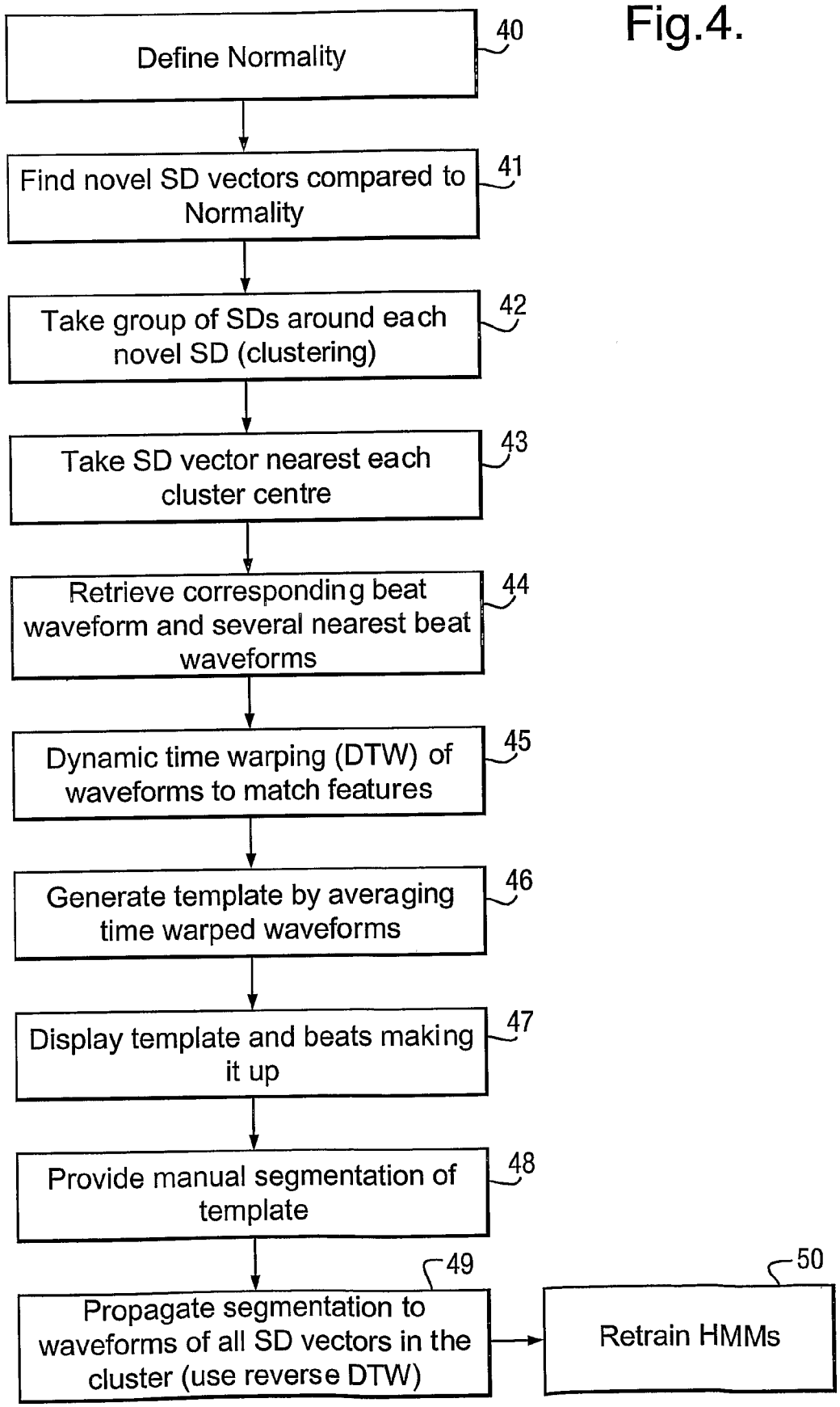
Figure 5:
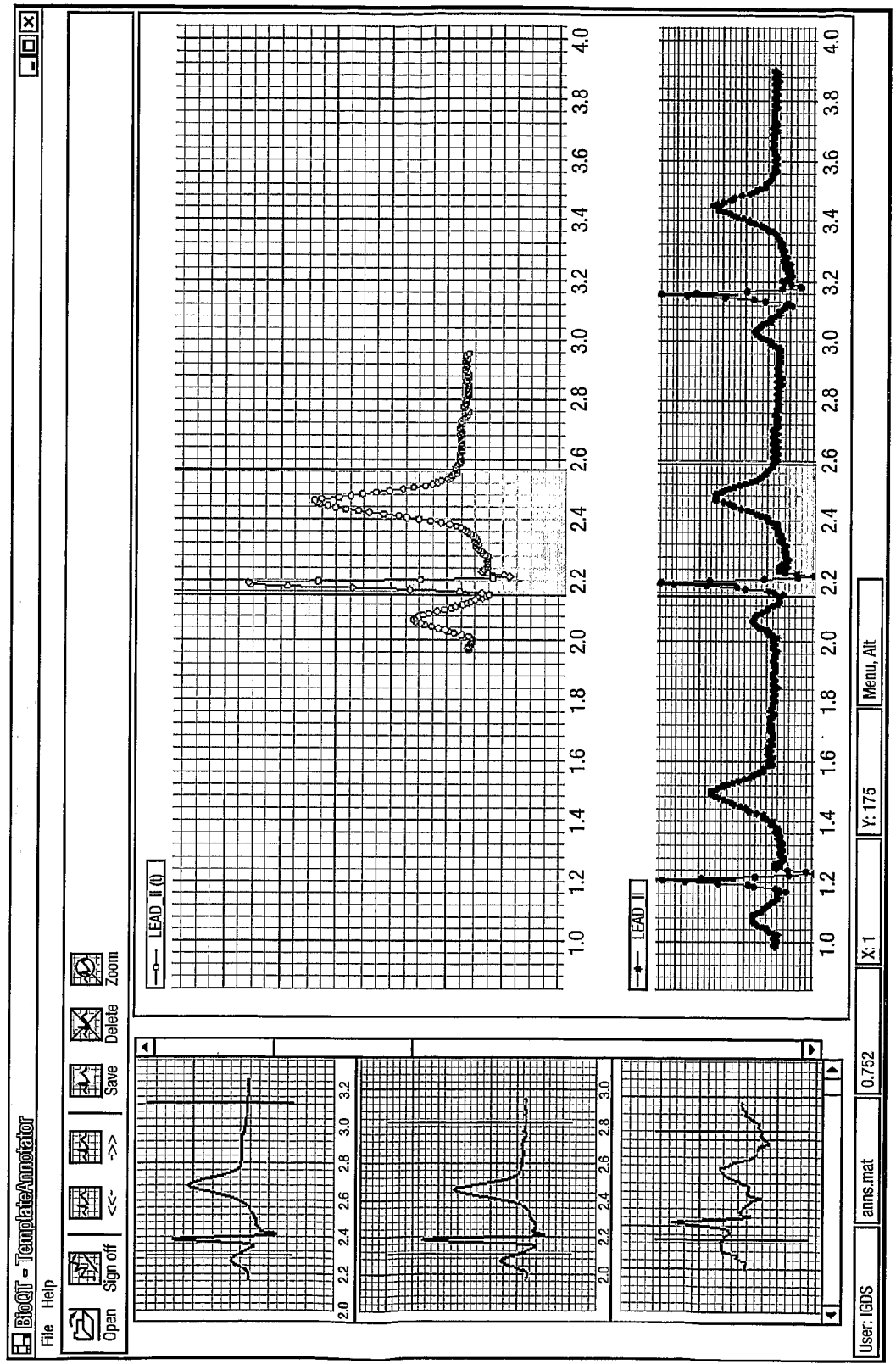
Figure 6:
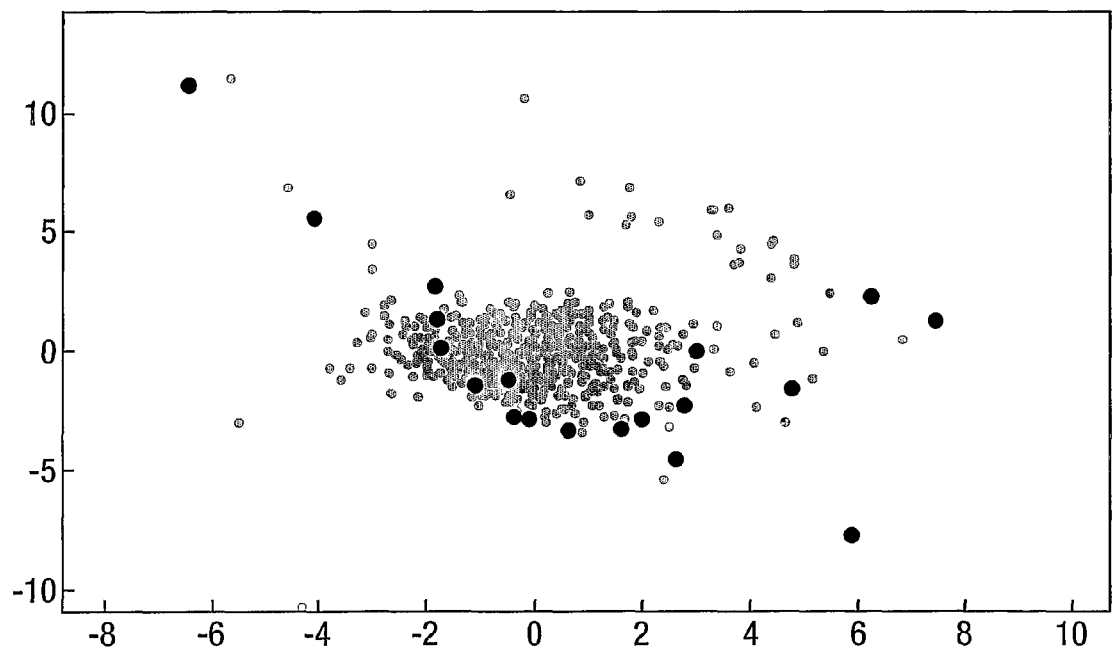
Figure 7:
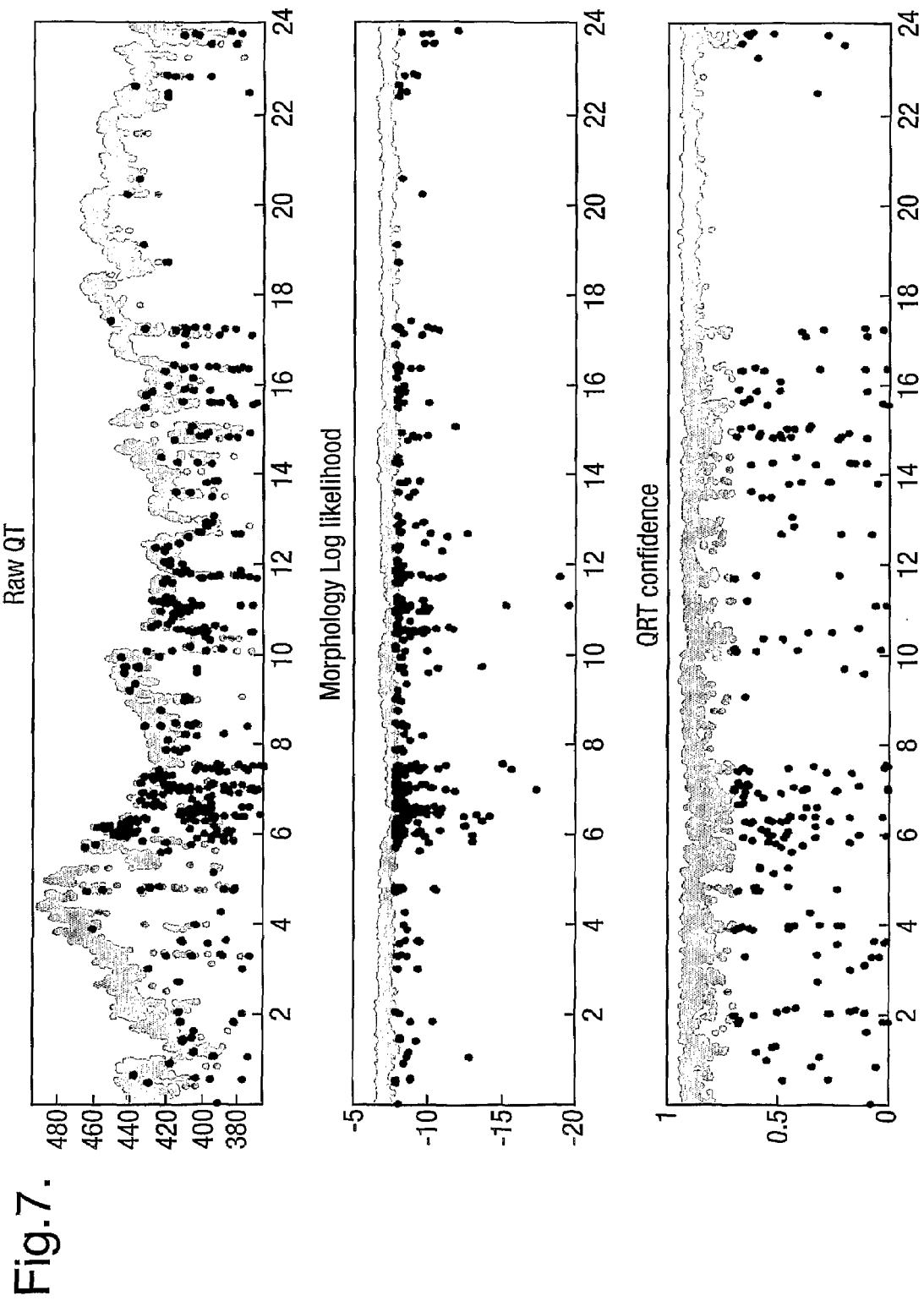
Figure 8:
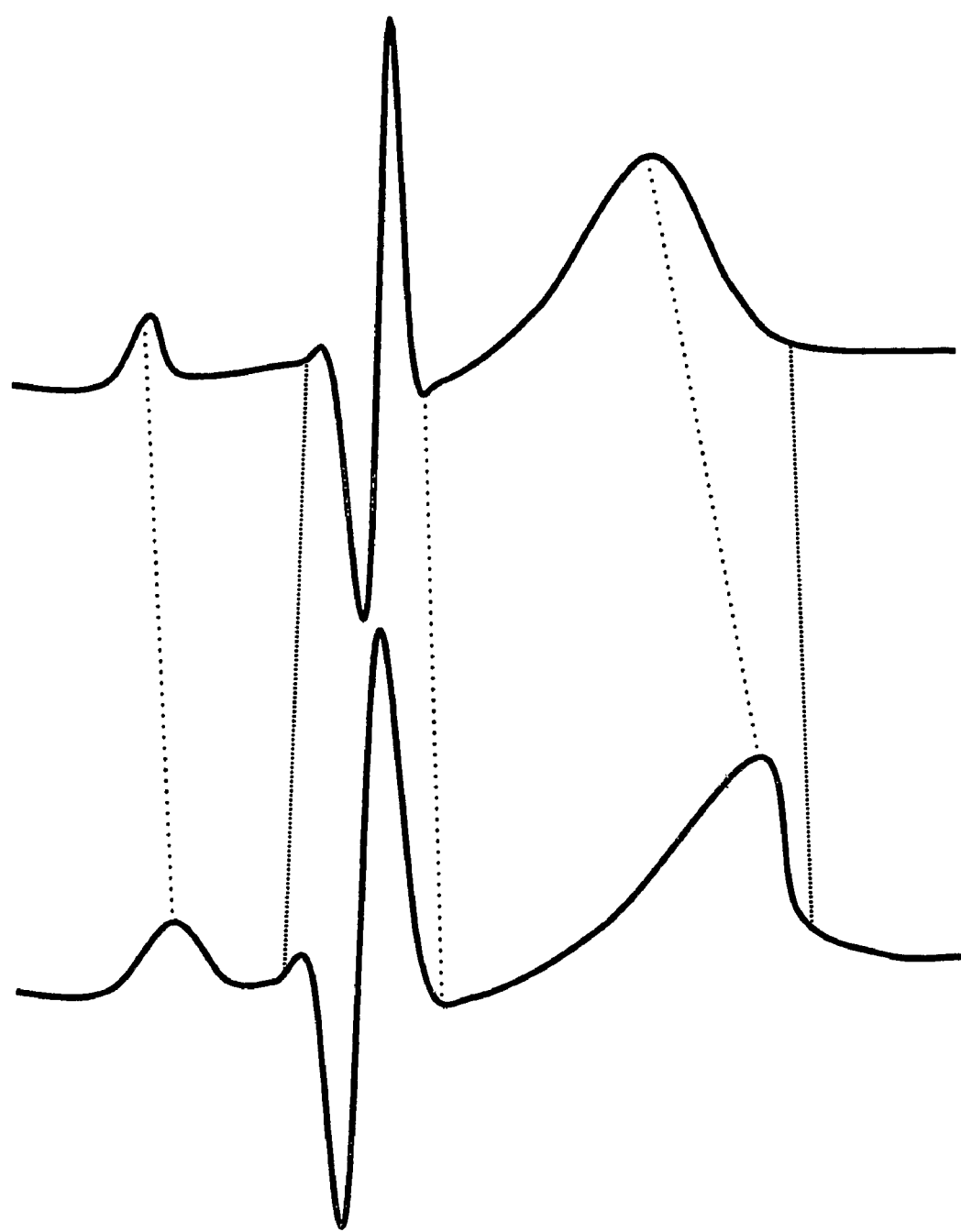
Figure 9:
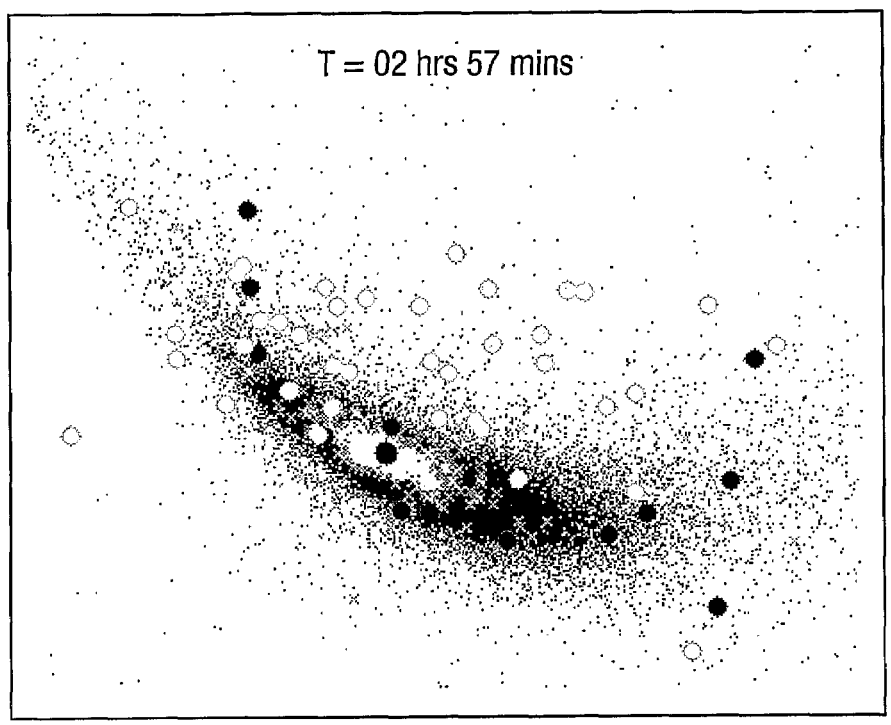
Figure 10:
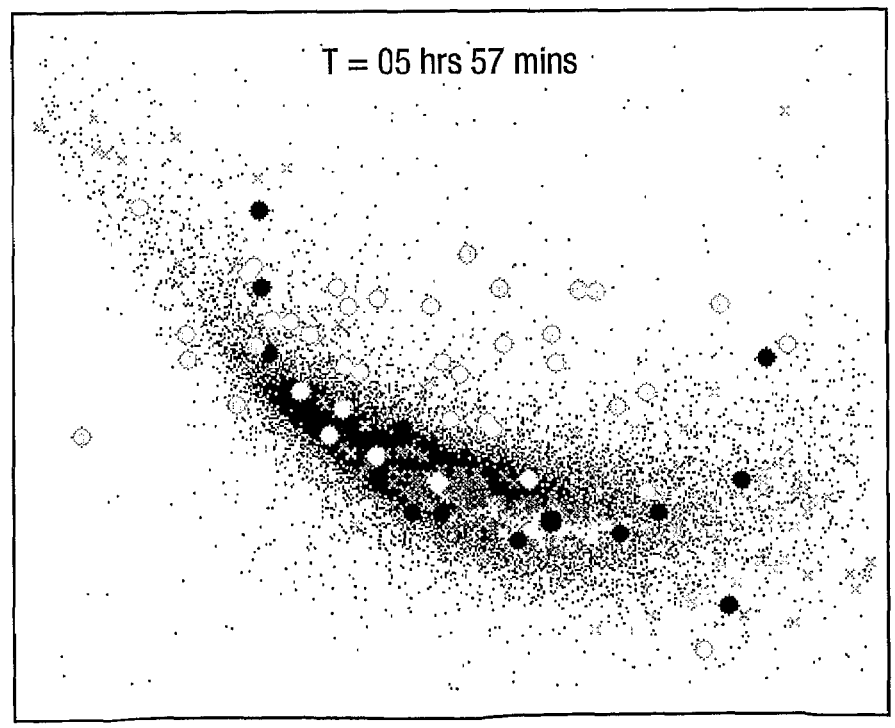
Figure 11:
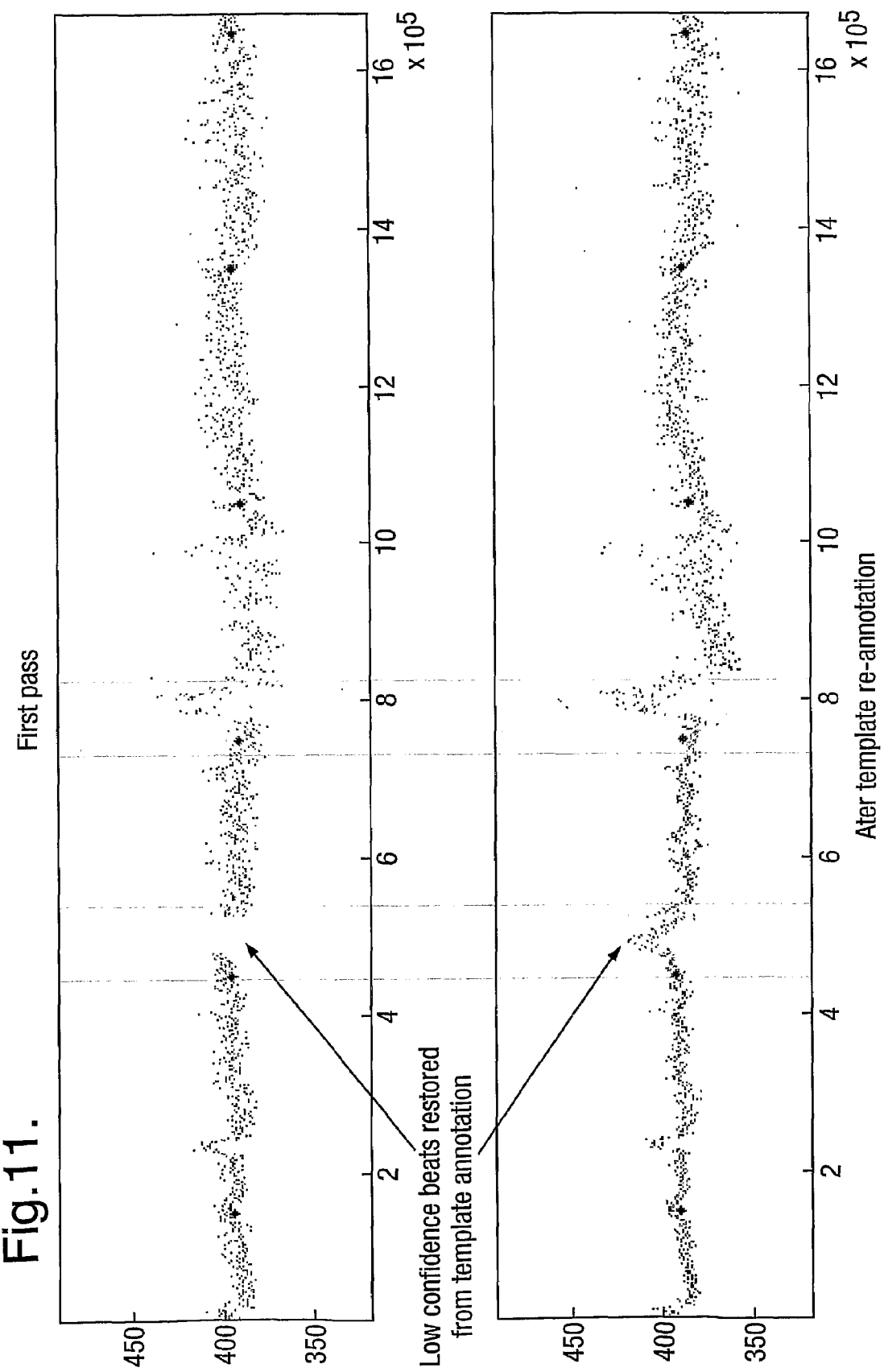
Figure 12:
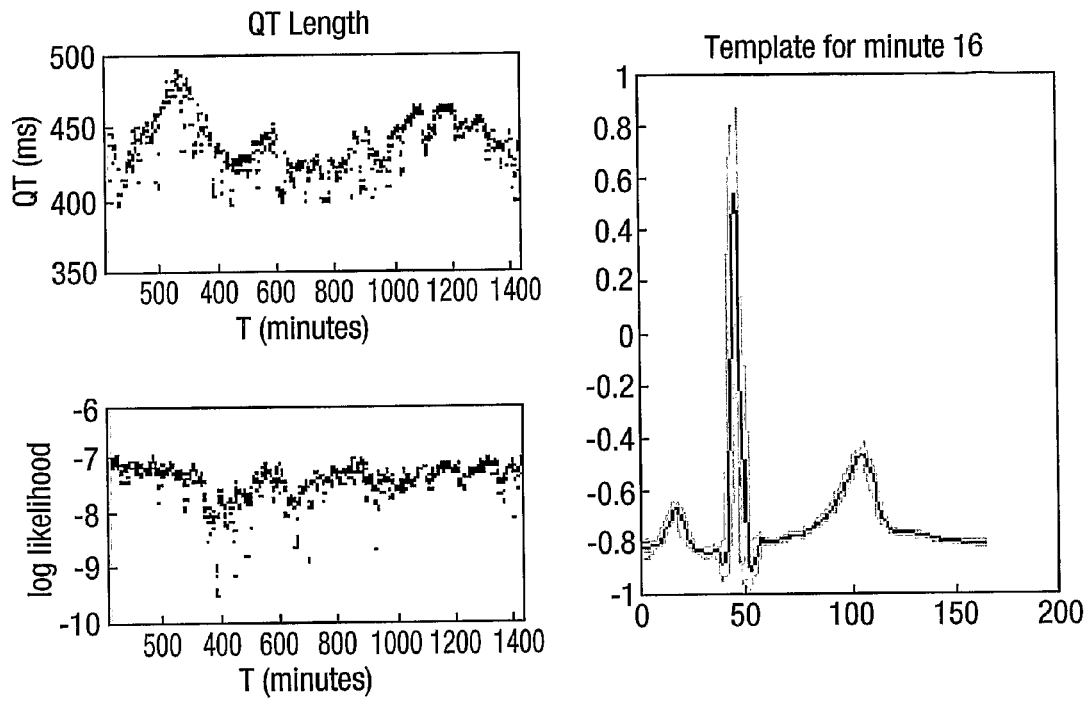
Figure 12:
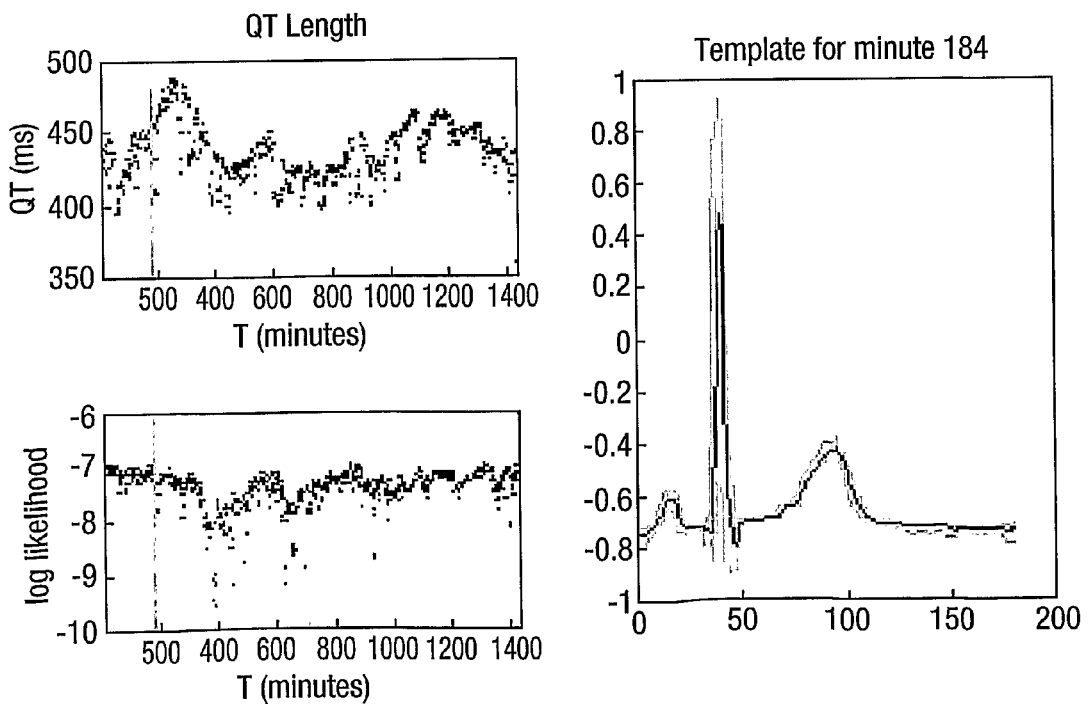
Figure 12:
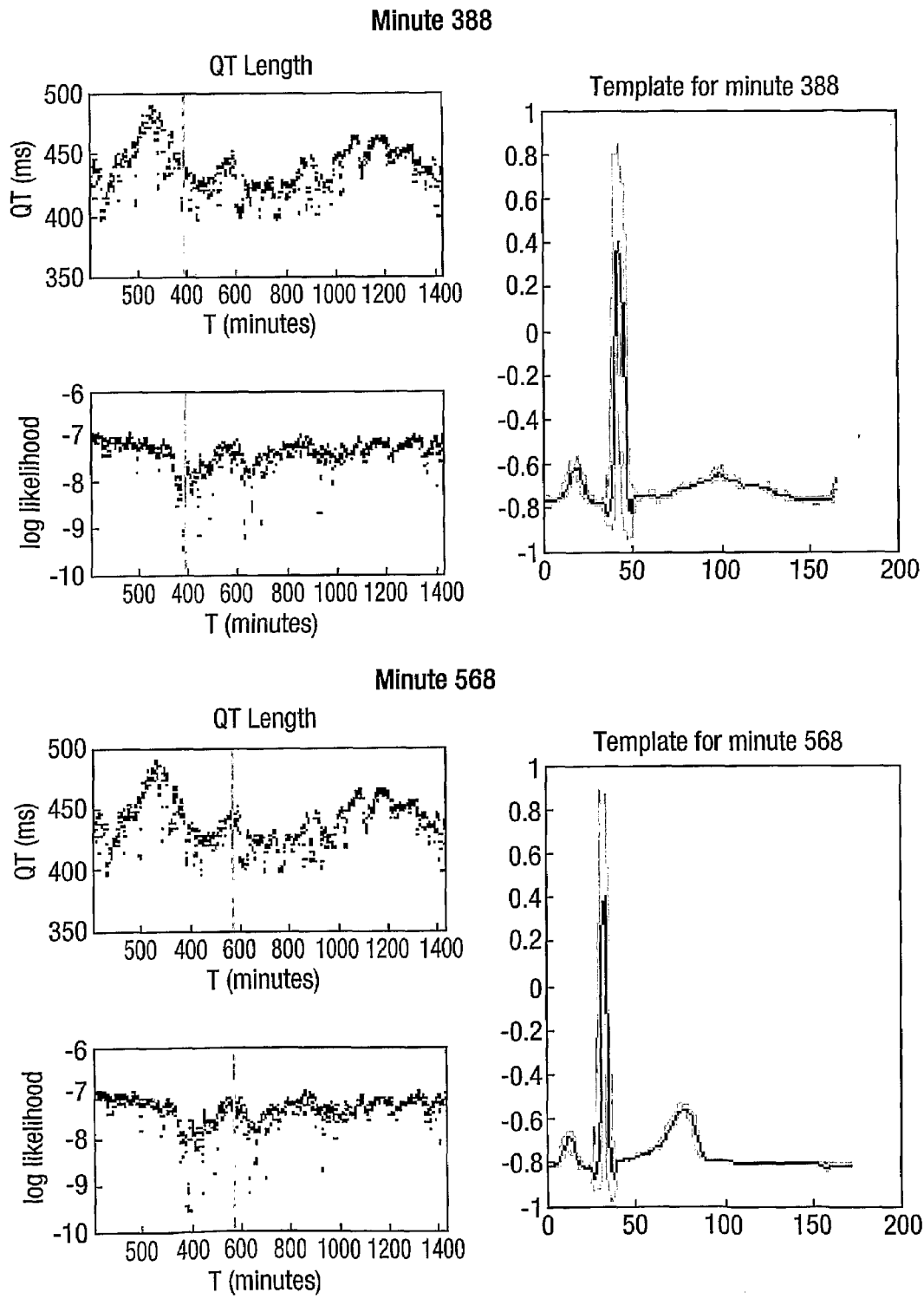
Figure 13:
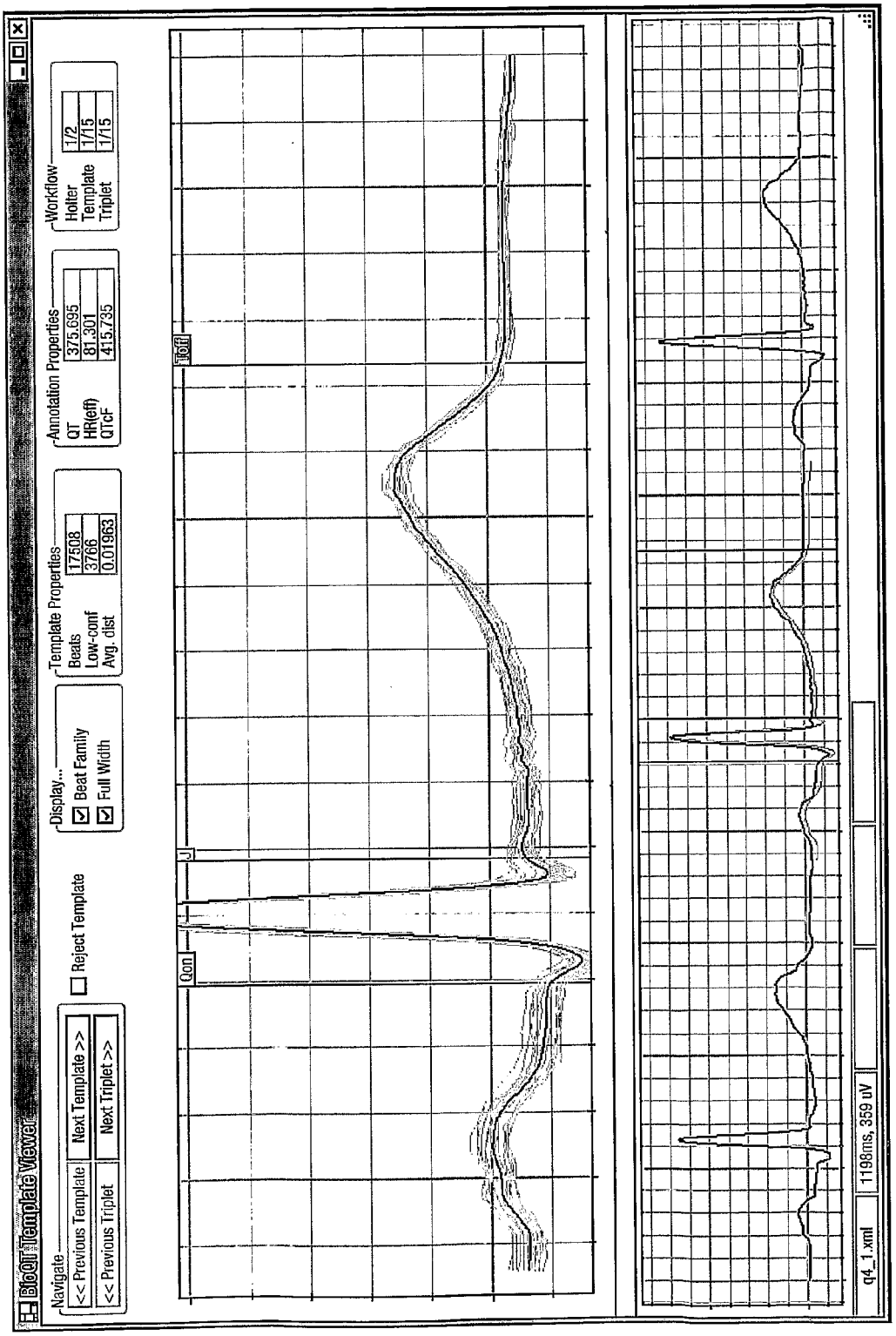

FIGS. 2B and C schematically illustrate the location of the scanning windows for the HMMs in one embodiment of the invention;

FIG. 3 is a flow diagram of a heartbeat templating process according to one embodiment of the invention;

FIG. 4 is a flow diagram illustrating the calculation of a quantitative shape description of part of an ECG waveform according to one embodiment of the invention;

FIG. 5 schematically illustrates the display of a heartbeat template for manual segmentation;

FIG. 6 is a dimensionality reduced plot of shape descriptors calculated in accordance of one embodiment of the invention;

FIG. 7 illustrates values of QT interval, morphology index and segmentation confidence for an example dataset;

FIG. 8 schematically illustrates the process of dynamic time warping;

FIGS. 9 and 10 show frames from an animation of the results of analysing an ECG using an embodiment of the invention;

FIG. 11 shows the QT interval measurements for a 24-hour Holter recording taken from a drug study before and after inclusion of re-annotated beats;

FIG. 12 illustrates four automatically generated beat templates alongside plots of QT interval and morphology novelty index for a subject's 24 hour Holter recording in a drug study; and FIG. 13 schematically illustrates an alternative to FIG. 5 of a display of a heartbeat template for manual segmentation.

An embodiment of the invention applied to the analysis of digitised electrocardiograms (ECGs) will now be described. This embodiment of the invention has two basic aims, the first being to provide a quantitative measure of the shape or morphology of the ECG waveform (more particularly the JT section) so that variations in cardiac function which result in changes of the waveform can be automatically detected and tracked, and secondly a way of rendering tractable the problem of allowing a cardiologist manually to segment waveforms which have not been segmented properly by an automatic segmentation algorithm bearing in mind the vast increase in amount of data caused by the move towards 24 hour monitoring of ECGs. This is achieved by defining and calculating a shape descriptor for the JT section of the ECG waveform, this descriptor then being used as the basis for detecting and tracking morphology changes and also for detecting novel morphologies which require manual segmentation and for deriving beat templates representative of closely-related morphologies to reduce the amount of manual segmentation required.

This embodiment of the invention is based on deriving a quantitative shape descriptor for the JT part of an ECG waveform, though of course the same techniques may be applied to describe the shape of other parts of the ECG waveform, and indeed to describe the shape of parts of other biomedical signals.

Figure 2C:
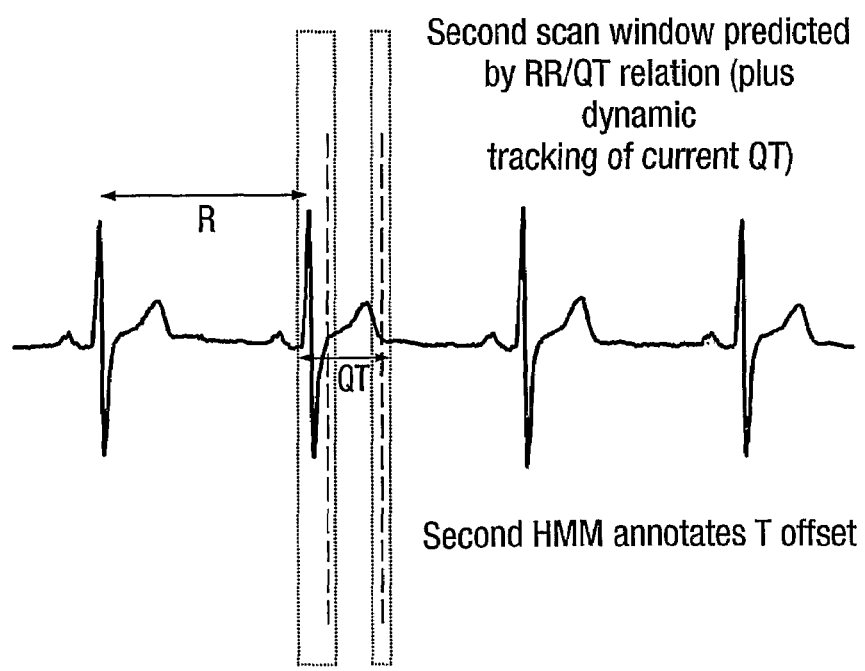

The first step in the process is to find the JT segment of the ECG waveform. This can be done by manual segmentation by a cardiologist, but FIG. 2 illustrates a method of finding the JT segment automatically using Hidden Markov Models in a technique analogous to the use of Hidden Markov Models to segment the whole waveform as described in WO 2005/107587 which is incorporated herein by reference. This is achieved by using two separate Hidden Markov Models, one of which detects the J point and one the $T_{offset}$, the two models being independent.

Figure 1:
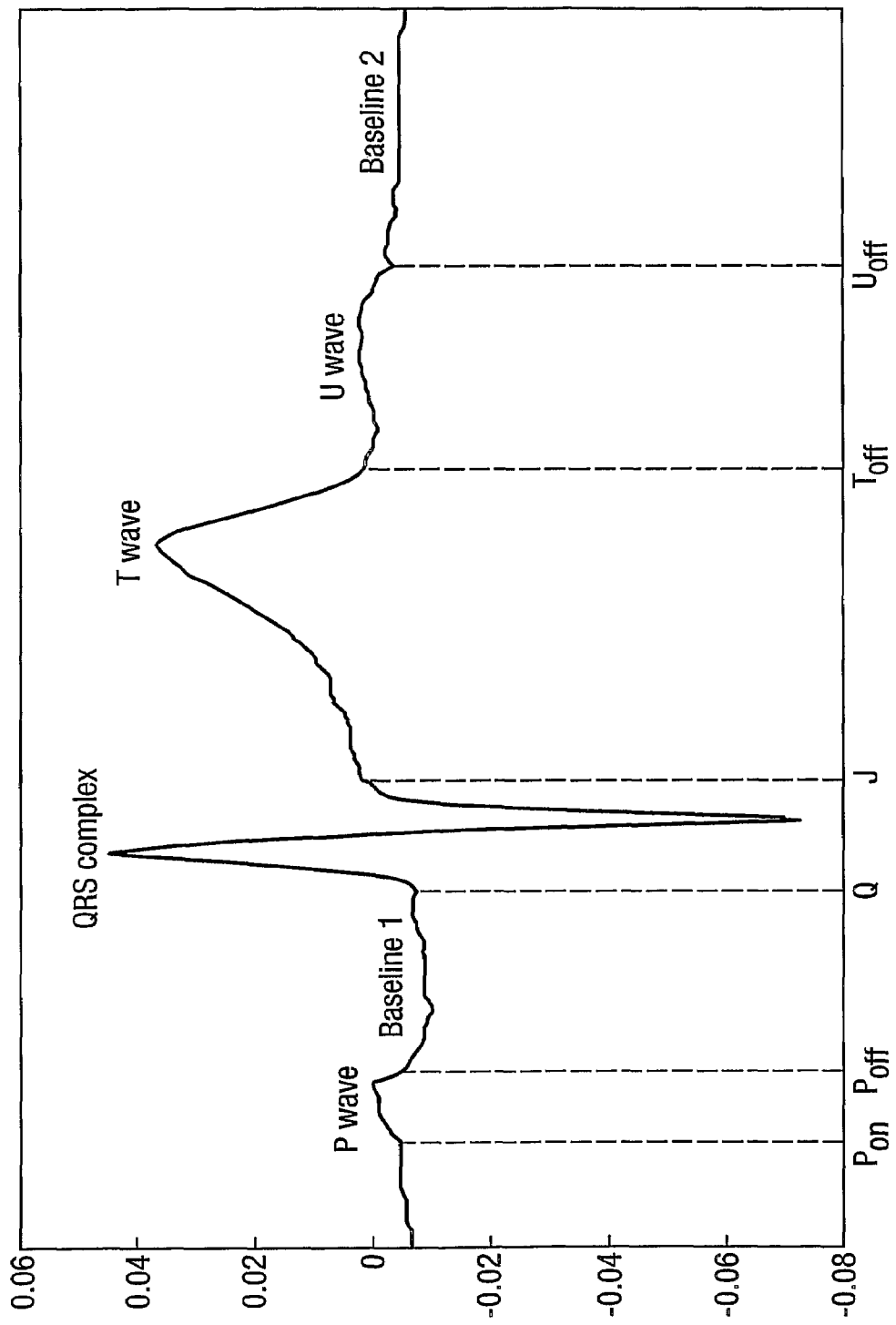
FIG. 1 shows a fully labelled ECG waveform.

In the following example the detection of the J point and $T_{offset}$ relies on the use of a Hidden Markov Model. The published patent application WO 2005/107587, and the papers Hughes N P and Tarassenko L. (2004). Automated QT Interval Analysis with Confidence Measures. *Computers in Cardiology*, pp. 31-34 and Hughes N P, Tarassenko L & Roberts S. (2004). Markov Models for Automated ECG Interval Analysis. *Advances in Neural Information Processing Systems*, vol. 16, Thrun S, Saul L & Scholkopf B (eds), MIT Press., which are incorporated herein by reference, describe how to apply a Hidden Markov Model for the entire extent of the human heart beat waveform as illustrated in FIG. 1. That technique detects the various time points in FIG. 1 corresponding to transitions between different states, in particular $P_{onset}$, $Q_{onset}$, J, and $T_{offset}$ points. It does this by processing the entire ECG waveform and having separate state models for the PR interval, the QRS interval, the T wave and the baseline region between the $T_{onset}$ point and the next P wave onset.

In this embodiment, the model to detect the J point has states corresponding to the segment of the waveform just prior to the QRS complex and also the waveform just after the J point (though as the QRS complex is invariant this state does not necessarily need to be included), while the model for detecting the $T_{offset}$ point has states corresponding to the waveform segments just prior to and just after the $T_{offset}$ point. The models are trained using a training set of manually annotated ECGs in a corresponding way to the full model described in WO 2005/107857, and the papers mentioned above.

Briefly, Hidden Markov Models comprise:

A Transition Model giving the initial probabilities of the hidden states, and a matrix of probabilities giving the probability of transition from one specific state to another specific state at the next observation in time. "Self-transitions" are when the state does not change between measurements.

A set of Observation Models, one for each of the states, each of which gives the probability of being in the said state, given the observations at any given time point.

In this embodiment, the "transition model" is easily derived from a set of manually annotated training data, which defines exactly which state (e.g. P wave, QRS complex, T wave) the model is in, as each state is defined by the time segment between the annotation points placed there by a clinician. Thus for each such segment, and on each manually annotated beat, we may count the number of self-transitions as being the overall number of time samples in that segment, and we also count the single transition from that state to the next one, given by the annotation point. This process is repeated for each state, and for each annotated beat, to give an overall count of samples in each state (from which the initial state probabilities are derived), and also the table counts of each type of transition (from which the transition probabilities may be derived).

The "observation models" may be based on Multivariate Gaussian Mixtures Models (see Bishop C. M. (1995) *Neural Networks for Pattern Recognition* (Chapter 2). OUP, Oxford, 1995 ISBN 0 19 853864) using a full covariance matrix, or an artificial neural network, such as the Multilayer Perceptron, that is trained to output posterior class probabilities, using the "softmax" output function (see Bishop C. M. (1995) *Neural Networks for Pattern Recognition* (pages 238-240). OUP, Oxford, 1995 ISBN 0 19 853864). The observation vectors consist of undecimated wavelet transform (UWT) coefficients and their derivatives (see Percival, D. B., and Walden, A. T., (2000) *Wavelet Methods for Time Series Analysis*. Cambridge University Press.). Training data for each of the state models is again extracted from the training set, with the corresponding state for a sample at a given time defined by the annotation points before and after that time. The Multivariate Gaussian Mixture models may be trained by the standard EM (Expectation-Maximization) algorithm (see Dempster, A. P., Laird, N., and Rubin, D (1977) Maximum Likelihood from incomplete data via the EM algorithm. *Journal of the Royal Statistical Society, B*, 39:-38), If a Multilayer Perceptron is to be used for the observation models, then these may also be trained by a non-linear optimization procedure, such as Scaled Conjugate Gradients. Example implementations of both the EM algorithm and the Scaled Conjugate Gradients non-linear optimization procedure are given in Nabney, I. T. (2002) *NETLAB—Algorithms for Pattern Recognition* (3) Springer, London ISBN 1-85233-440-1.

The trained Hidden Markov Model is applied to the input waveforms to segment them in the same way as the full model is applied in WO 2005/107587, except that each of the two models is only applied to a part of the ECG signal as explained in more detail below. For example, this may use the Viterbi Algorithm to find the most probable state sequence (i) and the probability of the sequence, the logarithm of which gives the confidence.

As illustrated in step 20 of FIG. 2 the J point forming the start of the JT segment is detected using the first Hidden Markov Model. The peak of the QRS complex, the R peak, can be located easily by using the standard Pan-Tompkins algorithm (see J. Pan and W. J. Tompkins, A Real-Time QRS detection algorithm, *IEEE Trans. Biomed. Eng.* BME-32(3) 230-236, 1985). The first Hidden Markov Model is scanned over a segment of the ECG waveform from just prior to the QRS complex to just after it to detect the transition from the QRS complex to the segment between the QRS complex and the T-wave. The transition between these two segments is denoted the J point.

Then, in step 21 of FIG. 2 the position of $T_{offset}$ is estimated using a relationship between the value of the QT interval and the R-R interval. This relationship can be obtained by analysing a patient's ECG, or a training set of ECGs to derive a static prediction model (in fact a linear relationship which allows calculation of the QT interval from the RR interval). However, it is preferred in this embodiment that instead of using a static model, a Kalman filter is used to track the QT value. Thus the Kalman filter maintains an estimate of the current QT interval, this estimate being corrected after each actual detection of the $T_{offset}$ point by a small factor proportional to the difference between the current estimate and the detected value.

In step 22 the second Hidden Markov Model comprising state models for the waveform segments prior to the $T_{offset}$ point and after the $T_{offset}$ point, is scanned over the section of the ECG waveform either side of the estimated $T_{offset}$ point. This returns an accurate location for $T_{offset}$, this being the end of the JT segment.

In step 23 the JT segment found by use of the first and second Hidden Markov Models is examined to derive the shape descriptor vector as will be described below.

The JT segment is smoothed, e.g. by using the technique of Principal Components Analysis. This is done by performing digital resampling of the JT segment to a standard length, being the mean of the lengths of the JT segments in the training data. Principal Components Analysis is essentially a projection onto an orthonormal axis set, where the projections onto the lower numbered axes account for more of the variance in the data than those onto the higher numbered axes. Smoothing is achieved by discarding the projections onto the higher numbered axes and only retaining a few of the lower numbered axes. The resultant points are then projected back into the original data space. Higher numbered axes tend to correspond to noise, so the Principal Components approach produces a smoothed version of the signal.

Having located the JT segment of the ECG waveform it is necessary then to derive a concise quantitative description of the shape of the waveform. In this embodiment the shape will be described by a plurality of shape descriptors. Each shape descriptor is a single number representing some aspect of the shape of the T wave such as initial slope, height of peak, number of turning points, etc. These numbers are assembled into a set which is termed a shape descriptor vector so that each beat has a single shape descriptor vector describing the shape of its T wave. In this embodiment the shape descriptors are based on the use of the "Analytic Signal" but other shape descriptors can of course be used. In signal processing, the analytic signal, or analytic representation, of a real-valued signal s(t) is defined by the complex signal:

$$s_a(t) = s(t) + j \cdot \hat{s}(t)$$

where ŝ(t) is the Hilbert transform of s(t) and j is the imaginary unit.

The definition of the Hilbert transform is as follows:

$$\hat{s}(t) = H\{s\} = (h*s)(t) = \int_{-\infty}^{\infty} s(\tau)h(t-\tau)d\tau = \frac{1}{\pi}\int_{-\infty}^{\infty} \frac{s(\tau)}{t-\tau}d\tau$$

where $$h(t) = \frac{1}{\pi \cdot t}$$

In the frequency domain, the Hilbert transform has the effect of shifting the positive frequency components by +90 degrees and the negative frequency components by −90 degrees.

The analytic signal may be computed trivially in the frequency domain by computing a one-sided FFT, (Fast Fourier Transform) where the negative frequency co components are set to zero, and then a complex valued time-domain signal is reconstructed by taking the inverse Fourier Transform.

In order to compute the shape descriptor vectors the analytic signal is decomposed into two real valued signals, namely the amplitude signal and the phase signal. The amplitude signal is simply the distance in the complex plane from each point in the time series to the origin and the phase signal is the angle between the line from the origin to the point in question and the x-axis.

Having calculated the amplitude and phase signals the shape descriptor in the present embodiment is defined by the following six quantities/components:

1. sine of the initial value of the phase signal;
2. cosine of the initial value of the phase signal;
3. initial rate of change (slope) of the phase signal;
4. final rate of change (slope) of the phase signal;
5. difference between the phase signal at start and end (this measures the number of turning points in the signal in a robust manner);
6. maximum value of the amplitude signal (gives roughly the height of the T-wave).

It is assumed that some form of amplitude or energy normalisation has been applied as part of the pre-processing of the ECG waveforms.

Thus in this embodiment the shape descriptor vector has these six components and thus the shape of each JT segment can be represented as a point in a six-dimensional shape descriptor vector space.

The shape descriptor vectors comprise a quantitative measurement of the shape of the JT segment. This can be used to track the shape throughout an ECG recording and monitor for changes.

This can conveniently be done by defining normality and then determining for any new shape descriptor vector whether it falls within the definition of normality, or if not how far it differs from normality.

In a batch learning process, in order to define normality a training set of manually annotated data representing normal waveforms is used. To produce the examples illustrated in FIGS. 6 and 7 of the attached drawings a training data set consisting of around 27,000 shape descriptor vectors computed from a corresponding number of manually annotated beats was used. Rather than using all 27,000 shape descriptor vectors directly in the model of normality, instead the shape descriptor vectors were used to define 500 shape descriptor template vectors by performing k-means clustering on the 27,000 original vectors. k-means clustering is a well known technique for clustering points in vector space. It is an iterative process of dividing the input points into k initial sets, finding the centroid of each set and then associating each point with the closest centroids. The centroids are recalculated and the process repeated. As a result the 500 shape descriptor template vectors are points in the shape descriptor vector space which are representative of a variety of normal shapes of JT segment. Any new shape descriptor vector can then be compared to this model of normality to determine whether it falls within that model, or whether it departs from normality (i.e. is novel). Two examples will be given for quantifying the degree of novelty, which can be regarded as a morphology index value.

A first, simple, example is to calculate the Euclidean distances between the new shape descriptor vector and each of the 500 shape descriptor templates. The template which is nearest (i.e. has the smallest value for the Euclidean distance) is termed the nearest neighbour. If the Euclidean distance to the nearest neighbour is greater than some threshold value, then the waveform is deemed to be novel.

A second way of quantifying novelty is by estimating the density of points in the shape descriptor vector space, from which a probability of normality of the new data point can be computed. This can conveniently be done by using a Parzen Windows estimate of the probability density. Then, in similar fashion to the first example, a threshold can be applied to the probability density value, or to the logarithm of that probability density.

Either the distance to the nearest neighbour or the log-probability density value can be used as a single numerical morphology index value to characterise how new a given waveform is. FIG. 7 illustrates the measured QT interval values, the morphology index values (log probability) and the confidence of the segmentation calculated using the Hidden Markov Models. It can be seen that there is a broad correspondence between regions of low confidence of segmentation and low morphology index value. This suggests that novel morphologies tend to correspond to drops in the confidence of the segmentation and it also means that the morphology index is capable of providing an additional measure of confidence in the ability of the automated algorithm to segment the waveform accurately.

The shape descriptor vectors may also be used to provide a more striking graphical display of morphology changes as illustrated in FIG. 6. This is achieved by performing a dimensionality reduction mapping on the shape descriptor vectors, such as Sarnmon's mapping, which is a process which takes the original six-dimensional shape descriptor vectors and maps them into a two dimensional space while minimising the change in inter-point distances in going from 6D to 2D space. This may be achieved by using the Neuroscale Algorithm as disclosed in D. Lowe and M. E. Tipping", "Neuro-Scale: novel topographic feature extraction using RBF networks", in *"Advances in Neural Information Processing Systems* 9. *Proceedings of the* 1996 *Conference"*, MIT Press, London, UK, 1997, ed. M. C. Mozer and M. I. Jordan and T Petsche, pages 543-9.

FIG. 6 illustrates the application of this to an example set of data. In FIG. 6 the blue smaller dots are the mapped versions of the 500 shape descriptor template vectors derived from the training set and representing the model of normality, and the larger red dots are cluster centres of waveforms from a patient's ECG where the log of the probability density (morphology index) fell below a threshold of −8. It can be seen that the red dots representing the new patient data extends for some distance outside the main region of normality.

Rather than the static display of FIG. 6, a particularly effective form of display is to provide an animation which shows the position of mapped shape descriptor vectors for a patient's ECG as a function of time, superimposed over the model of normality. In this way drifts in the morphology with time can easily be visualised. Two "frames" from such an animation are shown in FIGS. 9 and 10. FIG. 9 is at 2 hours 57 minutes from the start of the recording and FIG. 10 is at 5 hours and 57 minutes from the start of the recording. The screen shows as a group of blue dots the neuroscale mapping of the waveforms for a 24 hour Holter recording. Large grey dots show the cluster centres corresponding to the training data, and large black dots show cluster centres corresponding to novel morphologies. An animated "cloud" of yellow crosses tracks a time window, which can be between 10 and 30 minutes, of the projected shape descriptor vectors of all the beats within that window, and each frame of the animation advances the centre point of the window by a fixed number of beats. A large animated dot depicts the median X and Y points of the cloud. There follow two "frames" from the animation at different time points during the recording. It will be noted that in the second "frame", the crosses, corresponding to the annotation, is more widely dispersed, probably reflecting that during this part of the recording, the T-wave morphology was in a more novel part of feature space, resulting in more noisy measurements.

It was mentioned above that one of the problems of 24 hour monitoring of ECGs is that it generates a large amount of data, and although that data can be subject to automatic segmentation there is a corresponding increase in the number of beats in the data which cannot be segmented automatically. The shape descriptors described above and the concept of templating beats can be used to alleviate this problem.

FIG. 3 broadly illustrates this process. In a typical 24 hour Holter recording there may be up to 50,000 low confidence beats. By preparing templates corresponding to characteristic morphologies within these 50,000 beats, it is possible to produce typically 20-50 beat templates. It is these beat templates, or more particularly dynamic time warped versions of them (which as described below allow manual annotations to be propagated back to original waveforms) which can be reviewed by a cardiologist in a viewing application that allows, manual annotations to be applied to the template waveforms. These annotated templates can then be used to apply high confidence annotations to the waveforms whose shape descriptor vectors were closest to that particular template.

The procedure is illustrated in more detail in FIG. 4.

The process first requires a definition of normality in step 40, and this can be achieved as explained above by reference to a training set of ECGs (say the 27,000 manually annotated beats mentioned above) which produces 500 shape descriptor templates representing normality.

In step 41 novel shape descriptor vectors of a data set are found by comparing them to the model of normality using the nearest neighbour or probability approach mentioned above. Those which exceed the chosen thresholds are then regarded as "novel" T-wave morphologies compared to the original training set.

In step 42 these novel shape descriptor vectors are used to form a smaller number of candidates for novel templates by the process of k-means clustering. Thus each cluster consists of a group or family of shape descriptor vectors that are associated with one cluster centre which is the mean position of all the shape descriptor vectors in the cluster. Clear outliers are then rejected, namely those clusters which have only a few shape descriptor vectors associated with them. In practice these are generally due to flat or noisy T-waves.

In step 43, for each cluster the shape descriptor vector which is closest to the centre of the cluster is taken. This is regarded as being the most representative shape for that cluster. In step 44 the original waveform corresponding to that shape descriptor vector is retrieved and a window of the ECG signal around the R-peak location beginning just before the P-wave and ending just after the end of the T-wave is taken for the retrieved beat, and also a number of the neighbouring beats (e.g. five beats before and after) in that ECG recording. These will be used to define a template. If this section of the ECG recording is not satisfactory for some reason, a different shape descriptor vector which is close to the centre of the cluster can be taken and the ECG recording corresponding to it examined.

Recalling that the heart rate is modulated according to the breathing cycle, and may vary due to other influences, in step 45 the waveforms are corrected for this by dynamic time warping which is a very well established technique and has been used extensively in speech recognition, see, for example C. S. Myers and L. R. Rabiner, A comparative study of several dynamic time-warping algorithms for connected word recognition; *The Bell System Technical Journal*, 60(7):1389-1409, September 1981.

In this technique waveforms are adjusted by stretching or compressing along the time axis by matching corresponding points. The technique relies on the identification of corresponding points and in an ECG suitable points for the start and end points of the dynamic time warping are chosen to be a suitable time before the R-peak to around a similar time before the R-peak of the next waveform. This is in order to present a recognisable shape for the Cardiologist to use to apply manual annotations. FIG. 8 illustrates an example of two (hand-drawn) ECG waveforms which are to be subject to dynamic time warping. The aim is to compute a complete point for point mapping of time on one of the waveforms to time on the other waveform. Then, if one waveform has been segmented by finding, for example, the $Q_{onset}$ and $T_{offset}$ points, the second waveform can immediately be segmented at the same (warped) time points. One way of achieving dynamic time warping is to process both waveforms simultaneously by, at each time step, computing the next time sample of the output stretched waveform. This is either the value of the next time sample, or the current value. The decision on whether to take the next time sample or keep the current value is made by minimising the total sum of the square differences of the two stretched waveforms. This may be achieved efficiently using the Dynamic Programming Algorithm which allows an optimal solution to be computed by a single forward and backward pass through the data The time-warped versions of the beats are then averaged together in step 46 to make beat template. This template is displayed in step 47, together with the individual beats used to form it.

The template and individual beats are displayed using software which allows a cardiologist to annotate the template with labels corresponding to the start and end of the cardiological stages. This is illustrated schematically in FIG. 5. The list of templates available to annotate are in the scrolling window on the left of the screen. The display on the right hand side of the screen shows the template currently being edited by the Cardiologist. The cardiologist adjusts the position of the two vertical lines, indicating the Qonset and Toffset points with a mouse or with the keyboard cursor keys for fine adjustment. The lower graph shows a section of the actual segment of the ECG waveform that was used to generate the template. The vertical lines in the lower display are computed automatically by computing the point-for-point mapping between the template and the middle beat of the display by Dynamic Time Warping. The position of these lines is updated automatically as the Cardiologist adjusts the position of the annotation lines on the template.

Once the cardiologist has annotated the template, these annotations can be propagated back to perform segmentations of the individual beats, not only those beats used to form the template, but all of the beats in the cluster associated with that template. This involves reverse dynamic time warping to apply the segmentation in the time base of the original recording (as illustrated in FIG. 5). The segmented beats can then be stored and added to the database together with the beats that were originally segmented with high confidence by the automatic algorithm (i.e. those of normal shape).

An alternative example of the template display to the cardiologist is shown in FIG. 13. The top graph shows the template in black, with the family of beats used to generate it in light grey. All the beats in grey have been warped onto the template time axis using Dynamic Time Warping. The cardiologist can adjust the position of the annotation lines either by dragging the vertical lines with the mouse or using the cursor arrow keys on the keyboard to move by one pixel at a time. The currently active annotation (which moves with the arrow keys) is shown highlighted with its indicator in red (here $T_{off}$).

The lower trace in FIG. 13 shows a triplet of beats, the middle beat being one of the beats used to generate the template. The red trace shows the template warped onto the beat's time axis (the reverse mapping from the top graph). When the cardiologist moves the annotations, the corresponding positions on the lower trace (the green vertical lines) also move according to the Dynamic Time Warping mapping.

An example of the use of the re-annotation tool is shown in FIG. 11. The upper trace in FIG. 11 shows the QT interval measurements for a 24-hour Holter recording taken from a moxifloxacin study in which there are two periods in the study (shown shaded in FIG. 11) during which most of the beats have an unusual morphology. The confidence values associated with these beats are below the rejection threshold of 0.7 and so the QT interval measurements are not displayed. Once the cardiologist has reviewed and re-annotated the templates generated during these periods, each beat is automatically re-annotated using reverse dynamic time warping, producing the refined analysis of the lower trace, in which the re-annotated beats are re-inserted into the QT interval time series.

As indicated in step 50 it is also possible to use the newly segmented beats to re-train the Hidden Markov Models used in the original segmentation.

The above explanation is directed to analysing data sets in a batch learning mode based on a training set. However the techniques of template generation based on the shape descriptor vectors for beat families, and back-propagation of cardiologist annotations from the templates to beats in a family can be applied in an online learning mode or process as explained below.

In this mode the shape descriptor vectors are used in an on-line "templating algorithm" which assembles templates of the different T wave morphologies in the ECG recording. In this algorithm, the shape of the T wave is assumed to be normal at the start of the signal and so the initial template is the average 6-D shape descriptor vector from, say, the first fifteen minutes of the recording period. The 6-D shape descriptor for each subsequent JT segment is tested against this initial template. When the Euclidean distance in 6-D shape descriptor vector space between the shape descriptor and the template is greater than a given threshold, a new template is created: this template is the average waveform for the family of beats which has this novel T wave morphology. The shape of subsequent JT segments is now tested against both the initial template and the new template; again, when the Euclidean distance between a 6-D shape descriptor and its closest template (in 6-D space) is greater than the threshold, a new template is created. This process continues until the entire 24 hours of ECG data have been analyzed. The value of the threshold chosen controls the number of templates generated and experience acquired over a number of QT studies enables setting of this threshold empirically so that the number of templates generated remains below 20.

Such an approach may be appropriate in a study of a person's response to a drug or other stimulus, where the first fifteen minutes, say, of ECG, which might be before, or just after, administration of a drug or application of a stimulus, will tend to be normal. As the drug or other stimulus takes effect the T-wave morphology changes, generating new templates when the change exceeds the threshold. Eventually, if the patient returns to normal within the time of the recording, the beat morphology will return to normal and so the earlier templates will be applicable to the beats in the later parts of the recording. Thus typically each template will apply to a succession of similar shape individual beats occupying one or more time periods.

The cardiologist reviews and annotates the templates, and these annotations are propagated back to all of the beats in each template's family by dynamic time warping as described above. Thus by use of the templates it can be said that all beats in the recording have been reviewed indirectly by a cardiologist.

The templates can also be tested against a training set of data allowing automatic annotation in line with the annotations of the training set. In this case only templates which cannot be annotated with confidence need be referred to a cardiologist, or templates can be presented for review with a suggested annotation for checking by a cardiologist.

FIG. 12 illustrates exemplary results of such a process for a 24-hour Holter recording in a drug study. Four of the templates automatically generated by the online templating algorithm software can be seen in the figure: firstly, the initial template (minute 16), which is an ECG waveform with a normal T wave shape; then, at minute 184, another template is generated, which reveals a reduction in the height of the T wave. When the maximum morphology change occurs (minute 388), the T wave is almost entirely flat, as evidenced by the third template. By the time of the fourth template shown in the figure (minute 568), the T wave is well on its way to having recovered its original shape.

For each template, the same two panels displayed to the left of the template represent the QT interval (top panel) with the morphology novelty indicator shown below, both plotted against time (for the whole 24 hours of the study). The vertical line indicates for each panel the time at which the template is generated. The morphology novelty indicator continues to show a lower probability of normality (i.e. increasing degree of novelty) after the time at which the maximum QT prolongation is found. The greatest deviation from shape normality (the lowest value of the log likelihood for the morphology indicator) occurs at around 388 minutes into the recording, with the shallow and wide T wave of the third template.

The invention claimed is:

1. A method of analysing a biomedical signal having a repetitive signal feature, comprising the steps of segmenting each of a plurality of said repetitive signal features in the biomedical signal, analysing one or more of the segments to find the values of a plurality of parameters describing the shape of said one or more of the segments, said plurality of parameters constituting components of a shape descriptor vector for that segment, recording the values, and tracking changes in the said values through the biomedical signal; the method further comprising the step of defining normality for said shape descriptor vector, and calculating for each of said plurality of repetitive signal features the difference between its shape descriptor vector and normality.

2. A method according to claim 1 wherein the biomedical signal is an electrocardiogram and the repetitive signal feature is the heartbeat.

3. A method according to claim 2 wherein the step of analysing one or more of the segments comprises analysing the T-wave of the heartbeat, being the segment from the J point to the $T_{offset}$.

4. A method according to claim 3 wherein the J point is detected by use of a Hidden Markov Model comprising a state model for the waveform after the J point.

5. A method according to claim 3 wherein the $T_{offset}$ is detected by use of a Hidden Markov Model comprising state models for the T wave and the waveform after $T_{offset}$.

6. A method according to claim 5 wherein $T_{offset}$ is detected by the steps of: maintaining from beat to beat through the electrocardiogram an estimate of the QT interval based on a relationship between the QT interval and the heart rate, estimating the position of $T_{offset}$ from the estimated QT interval, and applying the Hidden Markov Model comprising state models for the T wave and the waveform after $T_{offset}$ to a portion of the electrocardiogram defined with respect to the estimated $T_{offset}$ position.

7. A method according to claim 6 wherein a Kalman filter is used to maintain said estimate of the QT interval.

8. A method according to claim 1 wherein normality is defined by shape descriptor vectors based on a plurality of repetitive signal features from training set.

9. A method according to claim 8 wherein the step of calculating for each of said plurality of repetitive signal features the difference between its shape descriptor vector and normality comprises calculating the distance in shape descriptor vector space between its shape descriptor vector and the nearest shape descriptor vector based on the training set.

10. A method according to claim 8 wherein the step of calculating for each of said plurality of repetitive signal features the difference between its shape descriptor vector and normality comprises calculating the density in the shape descriptor vector space of points derived from the training set, and calculating the probability of normality of the shape descriptor vector for each of said plurality of repetitive signal features.

11. A method according to claim 1 further comprising the step of displaying a morphology index value based on said difference.

12. A method according to claim 11 wherein changes in the morphology index value with time through the biomedical signal are displayed.

13. A method according to claim 1 further comprising the step of applying a dimensionality reduction mapping to the shape descriptor vectors and displaying the mapped shape descriptor vectors on a display.

14. A method according to claim 1 wherein said segmentation is performed automatically by a segmentation algorithm which in addition returns a value representing the confidence of the segmentation of each of said plurality of said repetitive signal features, and the method further comprises the steps of: selecting a proportion of said repetitive signal features having low segmentation confidence values and displaying said repetitive signal features, while providing for their manual segmentation by reference to the display.

15. A method of analysing a biomedical signal having a repetitive signal feature, comprising the steps of segmenting each of a plurality of said repetitive signal features in the biomedical signal, analysing one or more of the segments to find the values of a plurality of parameters describing the shape of said one or more of the segments, recording the values, and tracking changes in the said values through the biomedical signal, wherein said segmentation is performed automatically by a segmentation algorithm, and the method further comprises the steps of: selecting one or more of said repetitive signal features whose shape descriptor parameters depart from predefined normality by more than a predetermined threshold, and displaying said repetitive signal features, while providing for their manual segmentation by reference to the display.

16. A method according to claim 15 wherein said step of selecting one or more of said repetitive signal features whose shape descriptor parameters depart from predefined normality by more than a predetermined threshold comprises calculating the distance in shape descriptor vector space from the nearest shape descriptor vector of a predefined normal set, and comparing that to a predefined threshold.

17. A method of analysing a biomedical signal having a repetitive signal feature, comprising the steps of segmenting each of a plurality of said repetitive signal features in the biomedical signal, analysing one or more of the segments to find the values of a plurality of parameters describing the shape of said one or more of the segments, recording the values, and tracking changes in the said values through the biomedical signal, the method further comprising the steps of: selecting one or a group of waveforms from a first period in the biomedical signal and defining a first template based on the shape of said one or more waveforms, comparing subsequent waveforms in the signal to said template and generating a second template based on the shape of subsequent waveforms if their shape varies from the template by more than a predefined threshold, repeating the comparing and template generating steps until the end of the biomedical signal, and displaying said templates while providing for their manual segmentation by reference to the display.

18. A method according to claim 16 wherein for each of said selected one or more of said repetitive signal features whose shape descriptor parameters depart from predefined normality by more than a predetermined threshold, further of the signal features having similar shape descriptor parameters are selected to form respective groups of signal features, for each of said groups a template is defined based on the shape of the signal features in the group, and said template is displayed while providing for its manual segmentation by reference to the display.

19. A method according to claim 17 wherein the group comprises signal features whose shape descriptor vectors are within a predetermined distance of each other in shape descriptor vector space.

20. A method according to claim 18 wherein the group comprises signal features whose shape descriptor vectors are within a predetermined distance of each other in shape descriptor vector space.

21. A method according to claim 19 wherein the template is defined by repetitive signal features in the biomedical signal whose shape descriptor vector is closest to the centre of the group in shape descriptor vector space.

22. A method according to claim 20 wherein the template is defined by repetitive signal features in the biomedical signal whose shape descriptor vector is closest to the centre of the group in shape descriptor vector space.

23. A method according to claim 17 wherein the groups each comprise signal features which are temporally localised in the biomedical signal.

24. A method according to claim 18 wherein the groups each comprise signal features which are temporally localised in the biomedical signal.

25. A method according to claim 21 wherein said template is defined by taking an average of plural adjacent repetitive signal features in the biomedical signal whose shape descriptor vector is closest to the centre of the group in shape descriptor vector space.

26. A method according to claim 22 wherein said template is defined by taking an average of plural adjacent repetitive signal features in the biomedical signal whose shape descriptor vector is closest to the centre of the group in shape descriptor vector space.

27. A method according to claim 25 wherein said plural adjacent repetitive signal features are subjected to dynamic time warping to match signal features.

28. A method according to claim 26 wherein said plural adjacent repetitive signal features are subjected to dynamic time warping to match signal features.

29. A method according to claim 17 further comprising applying the manual segmentation of the template to the signal features of the corresponding group.

30. A method according to claim 18 further comprising applying the manual segmentation of the template to the signal features of the corresponding group.

31. A method according to claim 29 further comprising the step of applying reverse dynamic time warping to apply the manual segmentation of the template to the signal features of the corresponding group.

32. A method according to claim 30 further comprising the step of applying reverse dynamic time warping to apply the manual segmentation of the template to the signal features of the corresponding group.

33. A method according to claim 17 further comprising the step of retraining the segmentation algorithm using the manual segmentation of the template.

34. A method according to claim 18 further comprising the step of retraining the segmentation algorithm using the manual segmentation of the template.

* * * * *